United States Patent
Arhancet et al.

(10) Patent No.: US 10,227,551 B2
(45) Date of Patent: Mar. 12, 2019

(54) SULFUR-CONTAINING COMPOUNDS AS SOLVENTS

(71) Applicant: Novus International, Inc., St. Charles, MO (US)

(72) Inventors: Graciela B. Arhancet, St. Charles, MO (US); Scott A. Long, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 15/348,469

(22) Filed: Nov. 10, 2016

(65) Prior Publication Data

US 2017/0137756 A1    May 18, 2017

Related U.S. Application Data

(60) Provisional application No. 62/254,235, filed on Nov. 12, 2015.

(51) Int. Cl.
| | |
|---|---|
| *C11D 3/43* | (2006.01) |
| *C11D 3/34* | (2006.01) |
| *C11D 1/22* | (2006.01) |
| *C11D 3/10* | (2006.01) |
| *C07C 315/06* | (2006.01) |
| *C07C 319/26* | (2006.01) |
| *A61K 8/46* | (2006.01) |
| *A61Q 19/00* | (2006.01) |

(52) U.S. Cl.
CPC .............. *C11D 3/3445* (2013.01); *A61K 8/46* (2013.01); *A61Q 19/00* (2013.01); *C07C 315/06* (2013.01); *C07C 319/26* (2013.01); *C11D 1/22* (2013.01); *C11D 3/10* (2013.01); *C11D 3/349* (2013.01); *C11D 3/3427* (2013.01); *C11D 3/43* (2013.01); *A61K 2800/10* (2013.01); *A61K 2800/49* (2013.01)

(58) Field of Classification Search
CPC .................................................. C11D 3/3445
See application file for complete search history.

(56) References Cited

U.S. PATENT DOCUMENTS

| | | | |
|---|---|---|---|
| 2,787,595 A | 4/1957 | Webb | |
| 3,288,859 A | 11/1966 | Lyness et al. | |
| 3,290,254 A | 12/1966 | Anderson | |
| 3,329,617 A | 7/1967 | Doering | |
| 3,761,518 A * | 9/1973 | Haglid | C07C 317/00 426/648 |
| 3,850,987 A | 11/1974 | Haglid | |
| 4,000,318 A * | 12/1976 | Ferguson | A23K 20/105 426/2 |
| 4,095,029 A | 6/1978 | Fields | |
| 4,317,779 A | 3/1982 | Crawford | |
| 4,395,363 A | 7/1983 | Crawford | |
| 4,720,484 A | 1/1988 | Vincent et al. | |
| 5,294,605 A | 3/1994 | Houghten et al. | |
| 5,357,001 A | 10/1994 | Grosse-Bley et al. | |
| 5,386,056 A * | 1/1995 | Matsuoka | C07C 319/18 562/526 |
| 5,602,229 A | 2/1997 | Malabarba et al. | |
| 6,008,261 A | 12/1999 | Genova et al. | |
| 6,172,067 B1 | 1/2001 | Ito et al. | |
| 6,180,643 B1 | 1/2001 | Zablocki et al. | |
| 6,518,243 B1 | 2/2003 | Kahne et al. | |
| 6,528,541 B2 | 5/2003 | Robert | |
| RE39,403 E | 11/2006 | Robert | |
| 7,148,379 B2 | 12/2006 | Moller | |
| 7,250,443 B2 | 7/2007 | Desai et al. | |
| 7,795,180 B2 * | 9/2010 | Garcia-Mina Freire | C05F 11/10 504/319 |
| 8,546,601 B2 | 10/2013 | Buss | |
| 8,574,530 B2 | 11/2013 | Formentin | |
| 8,729,288 B2 | 5/2014 | Buss | |
| 9,133,113 B2 | 9/2015 | Degussa | |
| 9,169,203 B2 | 10/2015 | Grady | |
| 2001/0029308 A1 * | 10/2001 | Garrait | C07C 319/20 562/26 |
| 2009/0200511 A1 | 8/2009 | Allen et al. | |
| 2011/0201500 A1 | 8/2011 | Mertoglu | |
| 2013/0178540 A1 * | 7/2013 | Grady | C11D 1/002 514/785 |
| 2013/0209392 A1 | 8/2013 | Arhancet | |
| 2016/0010028 A1 | 1/2016 | Arhancet | |

FOREIGN PATENT DOCUMENTS

| | | |
|---|---|---|
| EP | 0576949 A1 | 6/1993 |
| FR | 2.229.698 A | 5/1974 |
| WO | 2010/082175 A2 | 7/2010 |
| WO | 2010/126794 A1 | 11/2010 |
| WO | 2017/083518 A1 | 5/2017 |

OTHER PUBLICATIONS

International Search Report and Written Opinion dated Mar. 13, 2017 in related International application No. PCT/US2016/061333, 11 pp.

Balg et al., "Inhibition of Helicobacter pylori Aminoacyl-tRNA Amidotransferase by Puromycin Analogues", J. Am. Chem. Soc., 2008, pp. 3264-3265, vol. 130, No. 11.

Clint et al., "Thermodynamics of Micellization of Homologous Series of n-Alkyl Methyl Sulphoxides and n-Alkyl(dimethyl)phosphine Oxides", J. Chem. Soc., Faraday Transactions 1, 1975, pp. 946-954, vol. 71.

(Continued)

*Primary Examiner* — Charles I Boyer

(74) *Attorney, Agent, or Firm* — Polsinelli PC

(57) ABSTRACT

Methods for using sulfur-containing compounds comprising short chain aliphatic ester or amide moieties as solvents and compositions comprising these compounds are provided.

22 Claims, No Drawings

(56) References Cited

OTHER PUBLICATIONS

Clint, "Micellization of Mixed Nonionic Surface Active Agents", J. Chem. Soc., Faraday Transactions 1, 1975, pp. 1327-1334, vol. 71.

Evans et al., "Nanomolar-Affinity, Non-Peptide Oxytocin Receptor Antagonists", Journal of Medicinal Chemistry, 1993, pp. 3993-4005, vol. 36, No. 25.

Hennaux et al., "Novel nonionic polymerisable surfactants based on sulfoxides. 1. Monomer synthesis and general surfactant behaviour", Colloid Polym. Sci., 2001, pp. 1149-1159, vol. 279.

Hennaux et al., "Novel nonionic surfactants based on sulfoxides. 2. Homo- and copolymers", Colloid Polym. Sci., 2003, pp. 807-814, vol. 281.

Ignasiak et al., "Characterization by mass spectrometry and IRMPD spectroscopy of the sulfoxide group in oxidized methionine and related compounds", Chemical Physics Letters, 2011, pp. 29-36, vol. 502.

Komori et al., "Structure Activity Relationships of Synthetic Antibiotic Analogues of chryscandin", The Journal of Antibiotics, 1985, pp. 1182-1203, vol. 38, No. 9.

Li et al., "High Throughput Synthesis of Peptide α-Thioesters Through the Use of "Volatilizable" Support", Journal of Combinatorial Chemistry, 2008, pp. 613-616, vol. 10, No. 5 (and Supporting Information).

Roenne et al., "Lipase-Catalyzed Esterification of Lactic Acid with Straight-Chain Alcohols", J. American Oil Chemists' Society, 2005, pp. 881-885, vol. 82, No. 12.

Sato et al., "Oxidation of sulfides to sulfoxides and sulfones with 30% hydrogen peroxide under organic solvent- and halogen-free conditions", Tetrahedron, 2001, pp. 2469-2476, vol. 57.

Yoshiizumi et al., "Studies on Scavenger Receptor Inhibitors. Part 1: Synthesis and Structure—Activity Relationships of Novel Derivatives of Sulfatides", Bioorganic & Medicinal Chemistry, 2002, pp. 2445-2460, vol. 10.

International Search Report and Written Opinion from related application, International Application No. PCT/US12/72016, dated Mar. 5, 2013, 9 pgs.

Sep. 2, 2016 Letter from MX associate with translation of Office action dated Aug. 30, 2016 in related Appln. No. MX/a/2014/008223, 3 pp.

Dec. 6, 2016 Letter from MX associate with translation of Office action dated Nov. 31, 2016 in related Appln. No. MX/a/2014/008223, 3 pp.

Translation of JP Office action dated May 17, 2016 in related Appln. No. JP 2014-551288, 2 pp.

Office action dated Dec. 18, 2014 from related U.S. Appl. No. 13/729,226, 6 pp.

European Search Report dated Dec. 14, 2015 from related EP Application No. 12864476.2, 8 pp.

Weissbach, Peptide Methionine Sulfoxide Reductase: Structure, Mechanism of Action, and Biological Function, Archives of Biochemistry and Biophysics, Jan. 15, 2002, pp. 172-178, vol. 397, No. 2.

* cited by examiner

SULFUR-CONTAINING COMPOUNDS AS SOLVENTS

CROSS REFERENCE TO RELATED APPLICATIONS

This application claims the benefit of U.S. Provisional Application No. 62/254,235, filed Nov. 12, 2015, which is hereby incorporated by reference in its entirety.

FIELD OF THE INVENTION

The present disclosure generally relates to the use of sulfur-containing compounds comprising short chain aliphatic ester or amide moieties as solvents.

BACKGROUND OF THE INVENTION

Solvents are liquids that have the ability to dissolve, suspend, or extract other materials. Solvents are used in a diversity of applications including paints and coatings, household and industrial cleaners, personal care products, pesticides, herbicides, and insecticides for agriculture, food processing, pharmaceuticals, inks, adhesives, and food packaging. Because of the wide use of solvents, there is a need for solvents that are water soluble and compatible with a wide variety of materials. Moreover, there is a need for solvents that comply with current and future volatile organic compounds (VOC) regulations.

SUMMARY OF THE INVENTION

Among the various aspects of the present disclosure encompasses a method for using a compound of Formula (I) as a solvent. The method comprises contacting at least one compound of Formula (I) with at least one solute to form a solution. The compound comprises Formula (I):

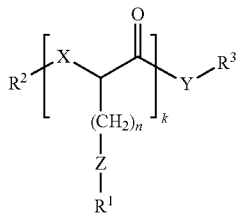

wherein:
- $R^1$ is hydrocarbyl or substituted hydrocarbyl;
- $R^2$ is hydrogen, hydrocarbyl, or substituted hydrocarbyl;
- $R^3$ is an aliphatic moiety having from one to twelve carbons in the principal chain when Z is S or $SO_2$, or an aliphatic moiety having from one to five carbons in the principal chain when Z is SO;
- X and Y independently are O or NH;
- Z is S, SO, or $SO_2$;
- k is an integer of 1 or greater; and
- n is an integer of 1 or greater.

Another aspect of the present disclosure provides a composition comprising at least one compound of Formula (I), at least one agent, and water. The compound of Formula (I):

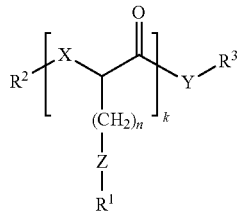

wherein:
- $R^1$ is hydrocarbyl or substituted hydrocarbyl;
- $R^2$ is hydrogen, hydrocarbyl, or substituted hydrocarbyl;
- $R^3$ is an aliphatic moiety having from one to twelve carbons in the principal chain when Z is S or $SO_2$, or an aliphatic moiety having from one to five carbons in the principal chain when Z is SO;
- X and Y independently are O or NH;
- Z is S, SO, or $SO_2$;
- k is an integer of 1 or greater; and
- n is an integer of 1 or greater.

A further aspect of the present disclosure encompasses a method for preparing a composition. The method comprises contacting at least one agent with at least one compound of Formula (I) to form the composition, the compound of Formula (I):

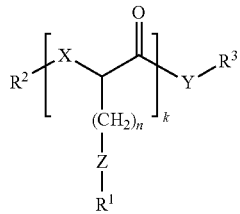

wherein:
- $R^1$ is hydrocarbyl or substituted hydrocarbyl;
- $R^2$ is hydrogen, hydrocarbyl, or substituted hydrocarbyl;
- $R^3$ is an aliphatic moiety having from one to twelve carbons in the principal chain when Z is S or $SO_2$, or an aliphatic moiety having from one to five carbons in the principal chain when Z is SO;
- X and Y independently are O or NH;
- Z is S, SO, or $SO_2$;
- k is an integer of 1 or greater; and
- n is an integer of 1 or greater.

Other features and iterations of the disclosure are described in more detail below.

DETAILED DESCRIPTION OF THE INVENTION

The present disclosure provides methods for using compounds comprising sulfur-containing moieties and short chain aliphatic ester or amide moieties as solvents. These solvents are compatible with a wide variety of materials and can be used in various applications and products including cleaning and personal care products, agricultural applications, and coating or paint formulations. Also provided herein are compositions comprising one or more of the sulfur-containing compounds comprising short chain aliphatic ester or amide moieties, at least one active agent, and water.

(I) Methods for Using Compounds of Formula (I) as Solvents

One aspect of the present disclosure provides a method for using compounds of Formula (I) as solvents, wherein a compound of Formula (I) comprises at least one sulfur-containing moiety and an short chain aliphatic ester moiety or a short chain aliphatic amide moiety. The method comprises contacting at least one compound of Formula (I), as detailed below, with at least one solute to form a solution. The compounds of Formula (I), therefore, can be used as solvents, co-solvents, emulsion solvents, processing solvents, active solvents, latent solvents, diluent solvents, and/or tail solvents.

(a) Compounds of Formula (I)

(i) Structure

The method comprises contacting at least one solute with at least one compound of Formula (I):

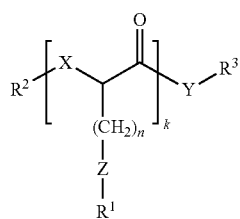

(I)

wherein:
$R^1$ is hydrocarbyl or substituted hydrocarbyl;
$R^2$ is hydrogen, hydrocarbyl, or substituted hydrocarbyl;
$R^3$ is an aliphatic moiety having from one to twelve carbons in the principal chain when Z is S or $SO_2$, or an aliphatic moiety having from one to five carbons in the principal chain when Z is SO;
X and Y independently are O or NH;
Z is S, SO, or $SO_2$;
k is an integer of 1 or greater; and
n is an integer of 1 or greater.

In various embodiments, $R^1$ may be alkyl, substituted alkyl, alkenyl, substituted alkenyl, alkynyl, substituted alkynyl, aryl, or substituted aryl. In some embodiments, $R^1$ may be $C_1$ to $C_6$ alkyl, optionally substituted, or $C_1$ to $C_6$ alkenyl, optionally substituted, wherein alkyl and alkenyl may be linear, branched, or cyclic. In certain embodiments, $R^1$ may be methyl, ethyl, propyl, isopropyl, butyl, tert-butyl, hexyl, cyclohexyl, and the like. In specific embodiments, $R^1$ may be methyl.

In certain embodiments, $R^2$ may be hydrogen, alkyl, alkenyl, alkynyl, aryl, substituted alkyl, substituted alkenyl, substituted alkynyl, or substituted aryl. For example, $R^2$ may be hydrogen, acyl, acyloxy, alkyl, alkyoxy, aminoalkyl, thioalkyl, alkenyl, alkenyloxy, aryl, aryloxy, amine, amide, ester, or ether. In some embodiments, $R^2$ may be hydrogen, methyl, ethyl, propyl, butyl, phenyl, benzyl, acetyl, propionyl, benzoyl, $(CH_2CH_2O)_pH$, $(CH_2CH(CH_3)O)_pH$, or a combination $(CH_2CH_2O)_pH$ and $(CH_2CH(CH_3)O)_pH$, wherein p is an integer of 1 or greater. For example, p may range from 1 to 20. In exemplary embodiments, $R^2$ may be hydrogen.

In general, $R^3$ is an aliphatic moiety having from one to twelve carbons in the principal chain. The aliphatic moiety may be alkyl, substituted alkyl, alkenyl, substituted alkenyl, alkynyl, or substituted alkynyl, and the aliphatic moiety may be linear or branched. In some embodiments, $R^3$ may be methyl, ethyl, propyl, isopropyl, butyl, isobutyl, pentyl, isopentyl, hexyl, isohexyl, ethylhexyl, heptyl, isoheptyl, methylheptyl, ethylheptyl, octyl, isooctyl, methyloctyl, ethyloctyl, nonyl, decyl, undecyl, dodecyl, ethenyl, propenyl, isopropenyl, butenyl, isobutenyl, hexenyl, isohexenyl, heptenyl, isoheptenyl, octenyl, isooctenyl, noneyl, ethynyl, propynyl, butynyl, isobutynyl, or hexynyl. In specific embodiments, $R^3$ may be $C_1$ to $C_{12}$ alkyl or $C_1$ to $C_{12}$ substituted alkyl.

In some embodiments, both of X and Y may be oxygen. In other embodiments, both of X and Y may be nitrogen (i.e., NH). In further embodiments, X may be oxygen and Y may be nitrogen. In additional embodiments, X may be nitrogen and Y may be oxygen.

In certain embodiments, Z may be sulfur. In other embodiments, Z may be sulfoxide (SO). In further embodiments, Z may be sulfone ($SO_2$).

In various embodiments, k may be an integer from 1 to 20. In specific embodiments, k may be 1, 2, 3, 4, 5, 6, 7, 8, 9, 10, or combination thereof. Thus, the compounds of Formula (I) may be monomers, dimers, trimers, tetramers, etc.

In some embodiments, n may be an integer from 1 to 20, from 1 to 10, or from 1 to 6. In certain embodiments, n may be 1, 2, 3, or 4. In specific embodiments, n may be 2.

In exemplary embodiments, $R^1$ may be methyl, $R^2$ may be hydrogen, X may be oxygen, Y may be oxygen or nitrogen, k may range from 1 to 6, and n may be 2. In certain iterations of these embodiments, $R^3$ may be $C_1$ to $C_8$ alkyl or $C_1$ to $C_8$ substituted alkyl, and Z may be sulfur. In other iterations of these embodiments, $R^3$ may be $C_1$ to $C_5$ alkyl or $C_1$ to $C_5$ substituted alkyl, and Z may be sulfoxide.

Table A presents exemplary compounds of Formula (I) in which $R^1$ is methyl, $R^2$ is hydrogen, n is 2, and k ranges from 1 to 6.

TABLE A

Exemplary Compounds of Formula (I)

| $R^3$ | X | Y | Z |
|---|---|---|---|
| methyl | O | O | S |
| ethyl | O | O | S |
| propyl | O | O | S |
| isopropyl | O | O | S |
| butyl | O | O | S |
| isobutyl | O | O | S |
| pentyl | O | O | S |
| isopentyl | O | O | S |
| hexyl | O | O | S |
| isohexyl | O | O | S |
| ethylhexyl | O | O | S |
| heptyl | O | O | S |
| isoheptyl | O | O | S |
| methylheptyl | O | O | S |
| ethylheptyl | O | O | S |
| octyl | O | O | S |
| isooctyl | O | O | S |
| methyloctyl | O | O | S |
| ethyloctyl | O | O | S |
| nonyl | O | O | S |
| decyl | O | O | S |
| undecyl | O | O | S |
| dodecyl | O | O | S |
| methyl | O | O | SO |
| ethyl | O | O | SO |
| propyl | O | O | SO |
| isopropyl | O | O | SO |
| butyl | O | O | SO |
| isobutyl | O | O | SO |
| pentyl | O | O | SO |
| isopentyl | O | O | SO |
| methyl | O | NH | S |

TABLE A-continued

Exemplary Compounds of Formula (I)

| R³ | X | Y | Z |
|---|---|---|---|
| ethyl | O | NH | S |
| propyl | O | NH | S |
| isopropyl | O | NH | S |
| butyl | O | NH | S |
| isobutyl | O | NH | S |
| pentyl | O | NH | S |
| isopentyl | O | NH | S |
| hexyl | O | NH | S |
| isohexyl | O | NH | S |
| ethylhexyl | O | NH | S |
| heptyl | O | NH | S |
| isoheptyl | O | NH | S |
| methylheptyl | O | NH | S |
| ethylheptyl | O | NH | S |
| octyl | O | NH | S |
| isooctyl | O | NH | S |
| methyloctyl | O | NH | S |
| ethyloctyl | O | NH | S |
| nonyl | O | NH | S |
| decyl | O | NH | S |
| undecyl | O | NH | S |
| dodecyl | O | NH | S |
| methyl | O | NH | SO |
| ethyl | O | NH | SO |
| propyl | O | NH | SO |
| isopropyl | O | NH | SO |
| butyl | O | NH | SO |
| isobutyl | O | NH | SO |
| pentyl | O | NH | SO |
| isopentyl | O | NH | SO |

In general, the compounds of Formula (I) disclosed herein have at least one chiral center, as denoted with an asterisk in the schematic below

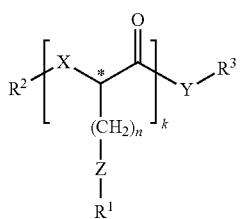

(I)

wherein $R^1$, $R^2$, $R^3$, X, Y, Z, n, and k are as defined above. The compounds disclosed herein may comprise additional chiral centers.

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

(ii) Mixtures of Compounds

In some embodiments a mixture of compounds of Formula (I) may be used in the method. For example, a mixture of monomer and/or oligomer compounds of Formula (I) k varies) may be used. Moreover, the mixture of compounds may have the same or different $R^3$ groups, and/or the mixture of compounds may have the same or different Z moieties.

(iii) Properties

Because the compounds of Formula (I) have both hydrophilic and hydrophobic moieties, they have the ability to dissolve or help dissolve other compounds. In general, the compounds of Formula (I) having five or fewer carbons in the principal chain of $R^3$ tend to be water soluble. Additionally, the compounds of Formula (I) are miscible with many common organic solvents. Accordingly, the compounds of Formula (I) can function as solvents or co-solvents in a wide variety of applications. Solvency power or the ability of one material to dissolve in another material can be estimated using Hansen's solubility parameters (i.e., δD for Dispersion (van der Waals), δP for Polarity (related to dipole moment), and δH for hydrogen bonding). These three parameters can be used as co-ordinates for a point in three dimensions also known as the Hansen space. A compound with a large Hansen space, therefore, is able to dissolve a large variety of compounds (e.g., both polar compounds such as alcohols and nonpolar compounds such as hydrocarbons).

(b) Solutes

A variety of solutes can be used in the methods disclosed herein, depending upon the properties of the compounds of Formula (I) and the type of solution to be made. Suitable solutes include, without limit, surfactants, fragrances, herbicides, fungicides, insecticides, pigments, binders, other solvents, wetting agents, thickening agents, foam control agents, dispersants, fillers, disintegrants, hydrotropes, linkers, pH regulating agents, chelating agents, preservatives, enzymes, optical brightening and/or bleaching agents, scale inhibitors, water softening agents, or combinations thereof.

In some embodiments, the solute may be one or more surfactants. The surfactant may be a nonionic surfactant, an anionic surfactant, or a cationic surfactant. Non-limiting examples of suitable nonionic surfactants (including zwitterionic surfactants that have no net charge) include alcohol ethoxylates, alkyl phenol ethoxylates (e.g., nonylphenyl ethoxylate), thiol ethoxylates, fatty acid ethoxylates, glycerol esters, hexitol esters, amine ethoxylates, alkylamide ethoxylates, and imide ethoxylates. Suitable anionic surfactants include, but are not limited to, alkyl sulfates, alkyl ether sulfates, sulfated alkanolamides, glyceride sulfates, dodecyl benzene sulfonates, alkylbenzene sulfonates, alpha olefin sulfonates, and sulfocarboxylic compounds. Non-limiting examples of suitable cationic surfactants include alkyl amines, quaternary alkyl ammoniums, ester amines, and ether amines.

In further embodiments, the solute may be one or more fragrances. Suitable fragrances include those formulated for personal care products (e.g., grooming, skin care, hair care, sun care, oral case, and the like), home care products (e.g., cleaners, degreasers, polishers, air fresheners, sanitizers, disinfectants, etc.), and fabric care products (e.g., laundry detergents, laundry pre-wash products, fabric softeners, and so forth). The fragrance may be "green" and/or non-allergenic. Suitable fragrances are well known in the art.

In additional embodiments, the solute may be one or more herbicides. Non-limiting examples of suitable herbicides include imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 OOH, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chloramben, chlorbromuron, chloridazon, chlorimuron-ethyl, chloroacetic acid, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-dichlorophenoxyacetic acid, daimuron, dalapon, dazomet, 4-(2,4-dichlorophenoxy)butanoic acid, desmedipham, desmetryn, dicamba, dichlobenil, dichlorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethalfluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, glufosinate-ammonium, glyphosate, glyphosinate, halosulfuron-methyl, haloxyfop, HC-252, hexazinone, imazamethabenz-methyl, imazamox, imazapyr, imazaquin, imazethapyr, imazosuluron, imidazilinone, indanofan, ioxynil, isoproturon, isouron, isoxaben, isoxaflutole, lactofen, lenacil, linuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachlor, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichloride, pebulate, pendimethalin, pentachlorophenol, pentanochlor, pentoxazone, petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, trietazine, trifluralin, triflusulfuron-methyl, and vernolate.

In still other embodiments, the solute may be one or more fungicides. Suitable fungicides include, without limit, carbamate fungicides such as 3,3'-ethylenebis(tetrahydro-4,6-dimethyl-2H-1,3,5-thiadiazine-2-thione), zinc or manganese ethylenebis(dithiocarbamate), bis(dimethyldithiocarbamoyl)disulfide, zinc propylenebis(dithiocarbamate, bis(dimethyldithiocarbamoyl)ethylenediamine, nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate, and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl) phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithioanthraquinone; copper 8-quinolinate, polyoxine; validamycin; cycloheximide; iron methanearsonate; diisopropyl-1,3-dithiolane-2-iridene malonate; 3-allyloxy-1,2-benzoisothiazol-1,1-dioxide; kasugamycin; blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethylaminopropyl)thiocarbamate hydrochloride; piomycin; S,S-6-methylquinoxaline-2,3-diyldithiocarbonate; complex of zinc and manneb; di-zinc bis(dimethyldithiocarbamate) ethylenebis (dithiocarbamate) and glyphosate; chlorothalonil-based fungicides, strobilurin-based fungicides such as azoxystrobin, pyraclostrobin, and trifloxystrobin; and triazole-based fungicide such as myclobutanil, propiconazole, tebuconazol, and tetraconazole.

In yet further embodiments, the solute may be at least one insecticide. Non-limiting examples of suitable insecticides include phosphoric insecticides such as O,O-diethyl O-(2-isopropyl-4-methyl-6-pyrimidinyl)phosphorothioate, O,O-dimethyl S-2-[(ethylthio)ethyl]phosphorodithioate, O,O-dimethyl O-(3-methyl-4-nitrophenyl)thiophosphate, O,O-dimethyl S—(N-methylcarbamoylmethyl) phosphorodithioate, O,O-dimethyl S—(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphophonate, O,O-diethyl-O-(5-phenyl-3-isooxazolyl)phosphorothioate, O,O-dimethyl O-(2,5-dichloro-4-bromophenyl) phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl] O,O-diethyl phosphorodithioate, 2-chloro-1-(2,4-dichlorophenyl)vinyl diethylphosphate, O,O-diethyl O-(3-oxo-2-phenyl-2H-pyridazine-6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl S—(N-ethoxycarbonyl-N-methylcarbamoylmethyl)phosphorodithioate, O,O-dimethyl S-[2-methoxy-1,3,4-thiadiazol-5-(4H)-onyl-(4)-methyl] dithiophosphate, 2-methoxy-4H-1,3,2-benzooxaphosphorine 2-sulfide, O,O-diethyl O-(3,5,6-trichloro-2-pyridyl) phosphorothiate, O-ethyl O-2,4-dichlorophenyl thionobenzene phosphonate, 5-[4,6-diamino-s-triazine-2-yl-methyl] O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O—N-(methylsulfinyl) phenyl phosphorothioate, O-ethyl S-propyl O-2,4-dichlorophenyl phosphorodithioate and cis-3-(dimethoxyphosphinoxy)N-methyl-cis-crotone amide; carbamate insecticides such as 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis(carbamoylthio)-2-(N,N-dimethylamino)propane hydrochloride and 2-diethylamino-6-methylpyrimidine-4-yl-dimethylcarbamate; and other insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl) 2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl) urea, and S-tricyclohexyltin O,O-diisopropylphosphorodithioate.

In other embodiments, the solute may be one or more pigments (or color agents). Pigments are finely ground particles or powders that provide coloring and hiding to paint formulations. The pigments may be prime pigments, which provide whiteness or color and hiding, or extender pigments, which ensure proper spacing of the prime pigments to avoid crowding and loss of hiding. In some embodiments, the prime pigment may be titanium dioxide or zinc oxide, the predominant white pigments. The prime pigments may also include organic or inorganic color pigments (or color agents). Color pigments or color agents are well-known in the art. Non-limiting examples color pigments include zinc yellow, benzidine yellow, chrome oxide green, phthalocyanine green, phthalocyanine blues, vermilion, pigment brown 6, red 170, dioxazine violet, carbon black, and iron(II) oxide. Suitable extender pigments (or extenders) include, without limit, clay (e.g., kaoline clay), silica, silicates, diatomaceous silica, quartz sand, calcium carbonate (also called limestone), barite, talc, and zinc oxide.

In further embodiments, the solute may be at least on binder (e.g., film former). Non-limiting examples of suitable binders include acrylic resins, latex (i.e., vinyl-acrylic or PVA) resins, vinyl acetate/ethylene (VAE) resins, polyester resins, phenolic resins, alkyd resins, urethanes resins, melamine resins, and epoxy resins.

In still other embodiments, the solute may be one or more additional solvents. The solvent may be organic or inorganic. Suitable organic solvents include, without limit, oxygenated solvents (such as alcohols, esters, ketones, glycol ethers, glycol ether esters, hydroxyethers, and alkoxy propanols), hydrocarbon solvents (such as aliphatic and aromatic hydrocarbons), and halogenated solvents (such as chlorinated hydrocarbons). Suitable inorganic solvents include water and ammonia.

In still other embodiments, the solute may be one or more wetting agents. Suitable wetting agents include but are not limited to nonionic surfactants such as polyoxyethylene surfactants, block co-polymer surfactants, alkyl polyglucoside surfactants, modified methyl capped block co-polymer surfactants, multibranched co-polymer surfactants, anionic surfactants, and cationic surfactants.

In alternate embodiments, the solute may be one or more thickening agents (i.e., rheological additives). Suitable thickening agents include without limit cellulosic ethers (such as hydroxycellulose, hydroxypropyl cellulose, hydroxymethylpropyl cellulose, hydroxyethyl cellulose, carboxymethyl cellulose, methylhydroxyethyl cellulose), polyvinylpyrrolidone, poly(vinylpyridine-N-oxide), acrylics, vinyl acrylics, bentonites, starches, gums, and combinations thereof.

In further embodiments, the solute may be at least one foam control agent (e.g., defoamer). Non-limiting examples of suitable foam control agents include defoamers based on ethylene oxide/propylene oxide copolymers, defoamers based on polymers with silicon backbones (e.g., silicone oils, polysiloxane, etc.), oil based defoamers (e.g., mineral oil, vegetable oil, long chain fatty acids, or fatty acid esters), and powder defoamers (e.g., silica).

In additional embodiments, the solute may be one or more dispersants. Suitable dispersants include without limit phosphonates, carboxymethyl inulin, sodium hexametaphosphate, sodium tripolyphosphate, tetrasodium pyrophosphate, potassium tripolyphosphate, and acrylic polymers.

In still other embodiments, the solute may be one or more fillers. Non-limiting examples of suitable fillers include cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, talc, modified starches, lactose, sucrose, mannitol, and sorbitol.

In yet further embodiments, the solute may be at least one disintegrant. Suitable disintegrants include without limit starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth.

In other embodiments, the solute may be one or more hydrotropes, which are compounds that improve the solubility of surfactants in aqueous solutions. Non-limiting examples of suitable hydrotropes include sodium toluenesulfonate, potassium toluene sulfonate, sodium xylene sulfonate, potassium xylene sulfonate, ammonium xylene sulfonate, sodium cumene sulfonate, ammonium cumene sulfonate, alkyl glucoside, complex coco imino glycinate, complex coco imino dipropionate, octyl imino dipropionate, phosphate ester potassium salt, and quaternary fatty methyl amine ethoxylate.

In alternate embodiments, the solute may be at least one linker, which are amphiphiles that are used to increase surfactant-water interactions (i.e., hydrophilic linkers) or surfactant-oil interactions (i.e., lipophilic linkers). Suitable hydrophilic linkers include without limit alkyl naphthalene sulfonates such as mono- or di-methyl naphthalene sulfonate and diisopropyl naphthalene sulfonate. Non-limiting examples of suitable lipophilic linkers include hydrocarbyl alcohols having 8 or more carbon atoms in the principal chain or their low ethoxylated derivatives.

In alternate embodiments, the solute may be one or more pH regulating agents. Non-limiting examples of suitable pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; and organic bases (such as, for example, pyridine, triethylamine monoethanol amine, diisopropylethylamine, N methylmorpholine, N,N dimethylaminopyridine).

In other embodiments, the solute may be at least one chelating agent. Suitable chelating agents include but are not limited to EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, and DTPMP.

In other embodiments, the solute may be at least one preservative. Non-limiting examples of suitable preservatives include antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, and sodium hypochlorite.

In certain embodiments, the solute may be one or more enzymes. Suitable enzymes include, but are not limited to, proteases, peptidases, subtilisin, mannanases, amylases, carbohydrases, and lipases.

In further embodiments, the solute may be at least one optical brightening agent and/or bleaching agent. Non-limiting examples of suitable optical brightening agents include triazine-stilbenes, coumarins, imidazolines, diazoles, triazoles, benzoxazolines, and biphenyl-stilbenes. In one embodiment, the optical brightening agent may be a sulfonated tetrabenzotetraazaaporphine derivative. The optical brightening agent may be used in combination with a polyol, such as polyethylene glycol, polypropylene glycol, or polyvinyl alcohol. Suitable bleaching agents include without limit hydrogen peroxide, peroxy acid, sodium perborate, sodium percarbonate, sodium hypochlorite, and sodium dichloroisocyanurate.

In certain embodiments, the solute may be one or more scale inhibitors. Non-limiting examples of suitable scale inhibitors include phosphonates, sodium hexametaphosphate, sodium tripolyphosphate, oxalic acid, phosphoric acid, sulfamic acid, and carboxymethyl inulin.

In further embodiments, the solute may be at least one water softening agent. Non-limiting examples of suitable water softening agents include sodium triphosphate, sodium tripolyphosphate, sodium carbonate, sodium silicate, zeolites, and citric acid.

(c) Reaction Conditions

The volume-to-mass ratio of the compound(s) of Formula (I) to the solute(s) may range from about 0.01:1 to about 100:1. In various embodiments, the volume-to-mass ratio of the compound(s) of Formula (I) to the solute(s) may range from 0.01:1 to about 0.1:1, from about 0.1:1 to about 1:1, from about 1:1 to about 10:1, or from about 10:1 to about 100:1.

In general, contact between the compound(s) of Formula (I) and the solute(s) occurs at a temperature from about 20° C. to about 70° C. In some embodiments, the contacting occurs at a temperature from about 20° C. to about 50° C. or from about 20° C. to about 30° C. The contacting can occur in the presence agitation, e.g., stirring, mixing, blending, rotating, and the like.

In embodiments in which the compound(s) of Formula (I) are contacted with more than one solute, the compound(s) of Formula (I) may be contacted with the solutes simultaneously or sequentially.

(d) Solutions

Upon contact of the compound(s) of Formula (I) with the solute(s), a solution is formed. A variety of solutions can be prepared. Non-limiting examples of suitable solutions includes home care products, fabric care product, personal care product, industrial or institutional cleaners, agricultural or landscaping products, and paint or coating formulations.

In some embodiments, the resultant solution may be a home care product, such as hard surface cleaner, glass and mirror cleaner, automatic dishwasher detergent, hand dishwashing liquid, all-purpose household cleaner, bathroom cleaner, heavy duty cleaner, degreaser, floor cleaner, floor polish, or air freshener. In still other embodiments, the solution may be an industrial or institutional cleaner or degreaser.

In further embodiments, the resultant solution may be a fabric care product, such as laundry detergent, laundry pre-wash product, fabric softener, fabric brightener, fabric freshener, stain remover, soft surface cleaner, wool cleaner, silk/delicate fabric cleaner, upholstery/rug cleaner, or stain repellent.

In alternate embodiments, the resultant solution may be a personal care product, such as a facial cleanser, body cleanser, hand cleaner, body wash, shower gel, bubble bath, shaving cream or gel, shampoo, hair conditioner, hair styling product, hair coloring product, hair shine product, baby cleaning product, baby lotion, cosmetic product, face cream, eye cream, anti-aging cream/serum, sun protecting lotion, body lotion, hand lotion, deodorant, antiperspirant, tanning lotion, toothpaste, dental gel, mouthwash, or other oral care product.

In still other embodiments, the resultant solution may be product for agricultural, forestry, or landscape applications. For example, the solution may be herbicide, fungicide, and/or insecticide solution for agricultural crops, animal enclosures, forests, golf courses, lawns, or landscape trees/shrubs.

In additional embodiments, the resultant solution may be a paint, resin, or coating formulation. The paint, resin, or coating formulation may comprise an acrylic-based emulsion, a vinyl acrylic-based emulsion, a styrene acrylic-based emulsion, a silicone resin emulsion, or combination thereof.

(II) Compositions

Another aspect of the present disclosure encompasses compositions comprising at least one compound of Formula (I), at least one agent, and water. The compositions may comprise one or more additional agents. The compounds of Formula (I) are detailed above in section (I)(a).

In some embodiments, the agent may be one or more surfactants, fragrances, or combinations thereof. Suitable surfactants, and fragrances are detailed above in section (I)(b). In such embodiments, the composition may be a home care product, a fabric care product, a personal care product, or an industrial or institutional cleaner. Such compositions may further comprise one or more additional agents chosen from surfactants, additional solvents, wetting agents, thickening agents, foam control agents, dispersants, fillers, disintegrants, hydrotropes, linkers, pH regulating agents, chelating agents, preservatives, enzymes, optical brightening and/or bleaching agents, scale inhibitors, water softening agents, fragrances, color agents, or combinations thereof.

In other embodiments, the agent may be one or more herbicides, fungicides, insecticides, or combinations thereof. Suitable herbicides, fungicides, and insecticides are described above in section (I)(b). Accordingly, the composition may be used as a product in agricultural and/or landscaping applications. The herbicide, fungicide, and/or insecticide compositions may further comprise at least one additional agent chosen from surfactant, additional solvent, wetting agent, thickening agent, foam control agent, dispersant, filler, disintegrant, hydrotrope, linker, pH regulating agent, chelating agent, preservative, or combination thereof.

In additional embodiments, the agent may be one or more pigments. Pigments are detailed above in section (I)(b). In such embodiments, the composition may be a paint formulation or a coating formulation. Said paint or coating formulations may further comprise one or more additional agents chosen from binders, additional solvents, surfactants, wetting agents, thickening agents, foam control agents, dispersants, fillers, disintegrants, chelating agents, preservative, fungicides, insecticides, or other biocides, or combination thereof.

The weight fraction of the one or more compounds of Formula (I) in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The weight fraction of the one or more agents in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The weight fraction of water in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The weight fraction of the one or more additional agents in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition (III) Methods for Preparing the Compositions A further aspect of the present disclosure provides methods for preparing the compositions disclosed herein. The method comprises contacting at least one agent with at least one compound of Formula (I) to form the composition. The compounds of Formula (I) are detailed above in section (I). Suitable agents are described above in section (II). The contacting generally occurs under the reaction conditions described above in section (I)(c). The compositions may further comprise one or more additional agents, as described above in section (II).

(IV) Processes for Preparing Compounds of Formula (I)

Still another aspect of the present disclosure encompasses processes for preparing the compounds of Formula (I). Persons skilled in the art understand that a variety of different processes may be used to prepare the compounds of Formula (I). Several processes are described below. Ester compounds may be prepared by a condensation reaction or a ring opening reaction. Amide compounds may be prepared by an amidation reaction. Additionally, compounds in which Z is sulfur may undergo one or more oxidation reactions to form sulfoxides or sulfones. The oxidation reaction(s) may occur before or after the esterification or amidation reactions.

(a) Esterification via Condensation

Ester compounds of Formula (I) may be formed by an esterification/polymerization process by which a compound of Formula (II) is contacted with an alcohol, $R^3OH$, to form a distribution of compounds of Formula (Ia) in which k varies. The reaction is diagrammed below:

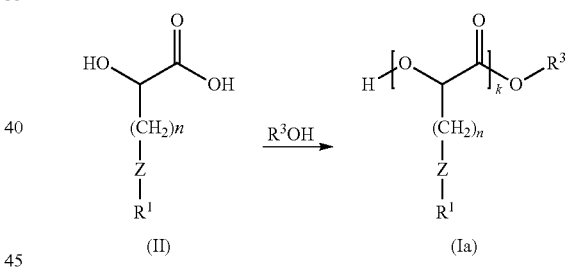

wherein $R^1$, $R^3$, Z, k, and n are as defined above in section (I).

The condensation reaction comprises contacting the compound of Formula (II) with an alcohol ($R^3OH$). Non-limiting examples of suitable alcohols include methanol, ethanol, 1-propanol, 2-propanol, 1-butanol, 2-butanol, 1-pentanol, 2-pentanol, 1-hexanol, 2-hexanol, 1-heptanol, 2-heptanol, 1-octanol, 2-octanol, 2-ethylhexanol, 3-ethylhexanol, 4-ethylhexanol, 1-methylheptanol, 2-methylheptanol, 3-ethylheptanol, 4-methylheptanol, and mixtures thereof.

The amount of alcohol that is contacted with the compound of Formula (II) can and will vary. In general, the mole-to-mole ratio of the compound of Formula (II) to $R^3OH$ may range from about 1:0.1 to about 1:10. In various embodiments, the mole-to-mole ratio of the compound of Formula (II) to $R^3OH$ may range from about 1:0.2 to about 1:8, from about 1:0.4 to about 1:6, from about 1:0.6 to about 1:5, from about 1:0.8 to about 1:4, from about 1:0.9 to about 1:3, or from about 1:1 to about 1:2.

In general, contact between the compound of Formula (II) and the alcohol is conducted in the presence of a catalyst.

The catalyst may be a chemical catalyst, such as a proton donor, an organometallic compound, such as tin compounds, or another chemical catalyst known in the art. Alternatively, the catalyst may be an enzyme catalyst, such as a lipase enzyme. Lipase enzymes can catalyze the formation (as well as hydrolysis) of ester linkages.

In embodiments in which the catalyst is a proton donor, a variety of proton donors may be used in the process. Non-limiting examples of suitable proton donor include acid salts (e.g., bisulfates, hydrosulfates), mineral acids (e.g., hydrogen halides such as hydrochloric acid, hydrobromic acid; halogen oxoacids such as hypochloric acid, chloric acid, perchloric acid, periodic acid; sulfuric acid; boric acid; nitric acid, phosphoric acid, etc.); sulfonic acids (e.g., methanesulfonic acid, p-toluenesulfonic acid); solid bound proton donors (e.g., Amberlyst 15, Amberlyst 35, and the like); ion exchange resins (e.g., Amberlite, Amberjet, Dowex, etc.); ionomers (e.g., polystyrene sulfonate, Nafion, Hycar and so forth); and ionic liquids having acidic characteristics.

The mole-to-mole ratio of the compound of Formula (II) to the proton donor catalyst can and will vary depending upon the identity of the proton donor. In general, the mole-to-mole ratio of the compound having Formula (II) to the proton donor may range from about 1:0.005 to about 1:0.25. In some embodiments, the mole-to-mole ratio of the compound of Formula (II) to the proton donor may be about 1:0.01, about 1:0.02, about 1:0.04, about 1:0.05, about 1:0.06, about 1:0.08, about 1:0.10, about 1:0.12, about 1:0.14, about 1:0.16, about 1:0.18, or about 1:0.20.

The reaction may be conducted in the absence of a solvent or in the presence of a solvent. In embodiments in which a solvent is present, the type of solvent may vary depending upon the reactants. Thus, the solvent may be a nonpolar solvent, a polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Non-limiting examples of suitable polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be toluene.

The volume-to-mass ratio of the solvent to the compound of Formula (II) can and will vary. Typically, the volume-to-mass ratio of the solvent to the compound of Formula (II) may range from about 1:1 to about 100:1. In various embodiments, the volume-to-mass ratio of the solvent to the compound of Formula (II) may range from about 1:1 to about 3:1, from about 3:1 to about 10:1, from about 10:1 to about 30:1, or from about 30:1 to about 100:1.

The reaction may be conducted at a temperature that ranges from about 30° C. to about 200° C. In certain embodiments, the temperature of the reaction may be about 40° C., 50° C., 60° C., 70° C., 80° C., 90° C., 100° C., 110° C., 120° C., 130° C., 140° C., or 150° C. In specific embodiments, the reaction may be conducted at a temperature from about 80° C. to about 150° C.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compound comprising Formula (II) and a significantly increased amount of the ester compound comprising Formula (Ia) compared to the amounts of each present at the beginning of the reaction.

The compounds of Formula (Ia) may be isolated from the reaction mixture by means known in the art. Suitable means include extracting, washing, precipitating, filtering, distilling, evaporating, drying, chromatography, and combinations thereof.

The yield of the compounds of Formula (Ia) can and will vary. In general, yield of the compounds will be at least about 20%, at least about 30%, at least about 40%, at least about 50%, at least about 60%, at least about 70%, at least about 80%, or at least about 90%.

(b) Esterification Via Ring Opening

Esters of Formula (I) also may be formed by a ring opening polymerization reaction by which a compound of Formula (III) is contacted with an alcohol, $R^3OH$, to form a distribution of compounds having Formula (Ia) in which k varies. The reaction is diagrammed below:

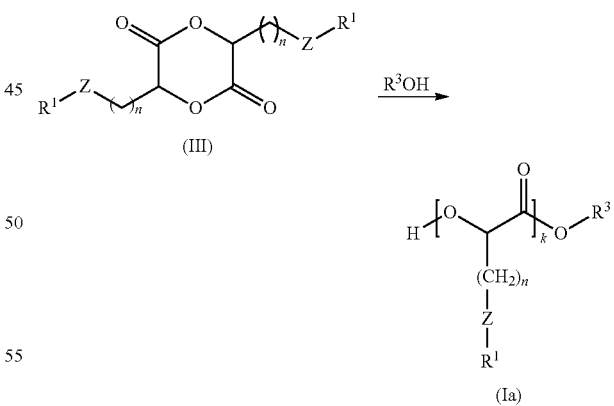

wherein $R^1$, $R^3$, Z, k, and n are as defined above in section (I).

The ring opening polymerization reaction comprises contacting the cyclic compound having Formula (III) with an alcohol ($R^3OH$). Suitable alcohols are detailed above in section (IV)(a). In general, the mole-to-mole ratio of the compound of Formula (III) to $R^3OH$ may range from about 1:0.1 to about 1:2. In various embodiments, the mole-to-mole ratio of the compound of Formula (III) to $R^3OH$ may range from about 1:0.2 to about 1:1, from about 1:0.3 to about 1:0.9, from about 1:0.4 to about 1:0.8, or from about 1:0.5 to about 1:0.7.

In general, contact between the compound having Formula (III) and the alcohol is conducted in the presence of a catalyst. Suitable catalysts and amounts to be included in the reaction mixture are detailed above in section (IV)(a). The reaction may be conducted in the absence or presence of a solvent, examples of which are detailed above in section (IV)(a). Suitable reaction temperatures, reaction times, optional isolation methods, and yields are described above in section (IV)(a).

(c) Amidation

Amides of Formula (I) may be prepared by process in which a compound of Formula (II) is contacted with an activation agent to form a compound of Formula (Ib), which is then contacted with an amine, $R^3NH_2$, to form the amide of Formula (Ic). The reaction is diagrammed below:

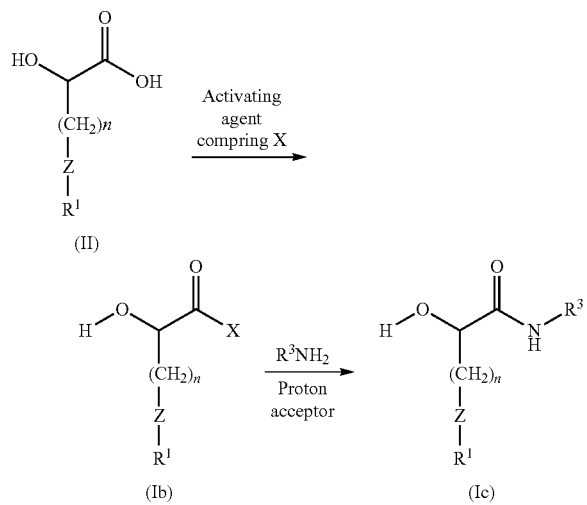

wherein $R^1$, $R^3$, Z, and n are as defined above in section (I) and X is a leaving group.

(i) Activation Step

The activation step of the process diagrammed above comprises contacting a compound of Formula (II) with an activating agent comprising a leaving group, X, to form the compound of Formula (Ib). A variety of activating agents may be used in this process. Non-limiting examples of suitable activating agents include thionyl halides (e.g., thionyl chloride, thionyl bromide, thionyl fluoride), acyl halides, acyl azides, anhydrides (e.g., carboxylic anhydrides, carbonic anhydrides, N-carboxy anhydrides), ester (e.g., alkyl esters, succinimidyl esters), and combinations thereof. In specific embodiments, the activating agent may be thionyl chloride.

The mole-to-mole ratio of the compound of Formula (II) to the activating agent can and will vary. In general, the mole-to-mole ratio of the compound of Formula (II) to the activating agent may range from about 1:1 to about 1:20. In various embodiments, the mole-to-mole ratio of the compound of Formula (II) to the activating agent may be about 1:2, 1:3, 1:4, 1:5, 1:6, 1:7, 1:8, 1:9, or 1:10.

Contact with the activating agent may occur in the absence or presence of a solvent. In general, the type of solvent used will depend upon the identity of the compound of Formula (II). Suitable nonpolar, aprotic, and protic solvents are detailed above in section (IV)(a). Typically, the volume-to-mass ratio of the solvent to the compound of Formula (II) may range from about 1:1 to about 60:1. In specific embodiments, the volume-to-mass ratio of the solvent to the compound of Formula (II) may range from about 4:1 to about 40:1.

Contact with the activating agent may occur at a temperature that ranges from about −10° C. to about 50° C. In certain embodiments, the temperature of the reaction may be about 0, 10, 20, 25, or 30° C. In one embodiment, the reaction may be allowed to proceed at about 0° C. In another embodiment, the temperature of the reaction may be room temperature. In still another embodiment, the reaction may be allowed to proceed for a first period of time at 0° C. and a second period of time at room temperature. Typically, the reaction will be conducted at atmospheric pressure.

The period of time of contact with the activating agent can and will vary. In general, the duration of time may range from about 0.5 hour to about 10 hours. In various embodiments, duration of the reaction may be about 1, 1.5, 3, 2.5, 3, 3.5, 4, 4.5 or 5 hours.

Upon completion of the reaction, a portion of the solvent may be removed from the reaction mixture using methods known to those skilled in the art.

In some embodiments, the alcohol moiety of the compound of Formula (II) may undergo a protection reaction prior to the activation step. During the protection reaction, the alcohol group is protected with a protecting group. Suitable protecting groups and means for attaching the protecting group are well known in the art. A variety of protecting groups and their addition and removal may be found in "Protective Groups in Organic Synthesis" by T. W. Greene and P. G. M. Wuts, John Wiley & Sons, 2006.

(ii) Amidation Step

The amidation step of the process diagrammed above comprises contacting the compound of Formula (Ib) with an amine of formula $R^3NH_2$ in the presence of a proton acceptor. Suitable amines include without limit methylamine, ethylamine, propylamine, isopropylamine, butylamine, hexylamine, heptylamine, octylamine, nonylamine, decylamine, undecylamine, and dodecylamine. The mole-to-mole ratio of the compound of Formula (Ib) and $R^3NH_2$ may range from 1:0.1 to about 1:10. In preferred embodiment, the mole-to-mole ratio of the compound of Formula (Ib) and $R^3NH_2$ may be about 1:1.

A variety of proton acceptors are suitable for use in this reaction. Non-limiting examples of suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), amines (such as, for example methylamine, dimethylamine, trimethylamine, ethylamine, diethylamine, triethylamine, propylamine, isopropylamine, diisopropylethylamine, and the like), organic bases (such as, for example, pyridine, N methylmorpholine, N,N dimethylaminopyridine), and mixtures of any of the above. In preferred embodiment, the proton acceptor may be triethylamine.

The mole-to-mole ratio of the compound of Formula (Ib) to the proton acceptor can and will vary depending upon the identity of the proton acceptor. In general, the mole-to-mole ratio of the compound of Formula (Ib) to the proton acceptor may range from about 1:0.01 to about 1:10. In various embodiments, the mole-to-mole ratio of the compound of Formula (Ib) to the proton acceptor may be about 1:0.5, 1:0.1, 1:0.5, 1:1, 1:1.5, 1:2, 1:3, 1:4, or 1:5. In a specific embodiment, the mole-to-mole ratio of the compound of Formula (Ib) to the proton acceptor may be about 1:2.

The amidation reaction may be conducted in the presence of a solvent. Suitable solvents and amounts thereof are detailed above in section (IV)(a).

The reaction may be conducted at a temperature that ranges from about −10° C. to about 50° C. In certain embodiments, the reaction may be allowed to proceed at about 0° C., 10° C., 20° C., 25° C., or 30° C. In a preferred embodiment, the reaction may commence at about 0° C. and slowly warm to room temperature over a period of time. In general, the reaction will be conducted at atmospheric pressure.

The duration of the reaction can and will vary. In general, the reaction may be allowed to proceed overnight (about 15-18 hours). Typically, however, the reaction may be allowed to proceed for a sufficient period of time until the reaction is complete, as determined by means well known to those of skill in the art.

The amide compound of Formula (Ic) may be isolated from the reaction mixture by means well known in the art. Suitable means include extracting, washing, precipitating, filtering, distilling, evaporating, drying, chromatography, and combinations thereof. In exemplary embodiments, the compound comprising Formula (Ic) may be isolated using chromatography.

The yield of the compound of Formula (Ic) can and will vary. In general, yield of the compound of Formula (Ic) will be at least about 30%, at least about 40%, at least about 50%, at least about 60%, at least about 70%, at least about 80%, or at least about 90%.

(d) Oxidation

Compounds of Formula (I) may undergo one or more oxidation reactions. An oxidation reaction is diagrammed below:

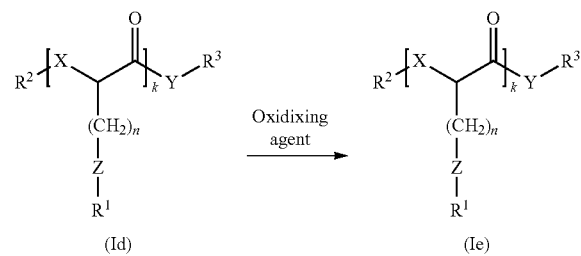

wherein $R^1$, $R^2$, $R^3$, X, Y, k, and n are as defined above in section (I), and wherein Z in the compound of Formula (Id) is S, and Z in the compound of Formula (Ie) is SO or $SO_2$.

A variety of oxidizing agents may be used in this process. Non-limiting examples of suitable oxidizing agents include peroxy acids (e.g., chloroperoxybenzoic acid, peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benezeneselenic acid, lead tetraacetate, osmium tetroxide, phosphomolybdic acid hydrate, pyridinium chlorochromate, pyridinium dichromate, quinolinium dichromate, and the like). and combinations thereof. In preferred embodiment, the oxidizing agent may be m-chloroperoxybenzoic acid or hydrogen peroxide.

The mole-to-mole ratio of the compound of Formula (Id) to the oxidizing agent can and will vary. In general, the mole-to-mole ratio of the compound of Formula (Id) to the oxidizing agent may range from about 1:0.1 to about 1:20. In various embodiments, the mole-to-mole ratio of the compound of Formula (Id) to the oxidizing agent may be about 1:0.8, 1:1.0, 1:1.2, 1:1.4, 1:1.6, 1:1.8, 1:2.0, 1:2.2, 1:2.4, 1:2.6, 1:2.8, 1:3.0, 1:3.2, 1:3.4, 1:3.6, 1:3.8, or 1:4.0. In specific embodiments, the mole-to-mole ratio of the compound of Formula (Id) to the oxidizing agent may be range from about 1:1 to about 1:3.

The oxidation reaction may be performed in the presence of a solvent. The solvent may be a nonpolar solvent, a protic solvent, or an aprotic solvent depending upon the nature of the reactants. Suitable solvents are detailed above in section (IV)(a). In some embodiments, the solvent may be dichloromethane, ethyl acetate, methanol, or water.

The volume-to-mass ratio of the solvent to the compound of Formula (Id) can and will vary. Typically, the volume-to-mass ratio of the solvent to the compound of Formula (Id) may range from about 1:1 to about 60:1. In various embodiments, the volume-to-mass ratio of the solvent to the compound of Formula (Id) may range from about 4:1 to about 40:1.

The oxidation reaction may be conducted at a temperature that ranges from about −10° C. to about 50° C. In certain embodiments, the temperature of the reaction maybe about 0° C., 10° C., 20° C., 25° C., or 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art. In this context, the final reaction mixture contains a significantly diminished amount of the compound of Formula (Id) and a significantly increased amount of the compound of Formula (Ie) compared to the amounts of each present at the beginning of the reaction.

The compound comprising Formula (Ie) may be isolated from the reactants in the reaction mixture by means well known in the art. Suitable means include extracting, washing, precipitating, filtering, distilling, evaporating, drying, chromatography, chiral chromatography, and combinations thereof. In certain embodiments, the compound comprising Formula (Ie) may be isolated using chromatography.

The yield of the compound comprising Formula (Ie) can and will vary. In general, yield of the compound comprising Formula (Ie) will be at least about 40%, at least about 50%, at least about 60%, at least about 70%, at least about 80%, at least about 90%, at least about 95%, at least about 96%, at least about 97%, at least about 98%, or at least about 99%.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is N hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

As used herein, the term "aliphatic" refers to a hydrocarbyl group in which the carbon atoms are linked in open chains, i.e., either linear or branched but not cyclic. Alkyl, alkenyl, and alkynyl groups, optionally substituted, are aliphatic.

The term "alkyl" as used herein describes groups containing from one to thirty carbon atoms in the principal chain. They may be straight or branched chain or cyclic and include methyl, ethyl, propyl, isopropyl, butyl, hexyl and the like.

The term "alkenyl" as used herein describes groups containing from two to thirty carbon atoms in the principal chain and further comprising at least one carbon-carbon double bond. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups containing from two to thirty carbon atoms in the principal chain and further comprising at least one carbon-carbon triple bond. They may be straight or branched chain and include ethynyl, propynyl, butynyl, isobutynyl, hexynyl, and the like.

The term "amide" as used herein describes a compound comprising a carbonyl-nitrogen linkage.

The term "aminoacyl" refers to an amino acid residue.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, piperidyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic.

The term "protecting group" as used herein denotes a group capable of protecting a functional group (e.g., an alcohol or an amine), wherein the protecting group may be removed, subsequent to the reaction for which protection is employed, without disturbing the remainder of the molecule. Non-limiting examples of suitable alcohol protecting groups include acetyl (Ac), benzoyl (Bz), benzyl (Bn, Bnl), β-methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), trityl (triphenylmethyl, Tr), silyl ethers (e.g., trimethylsilyl (TMS), tert-butyldimethylsilyl (TBDMS), tri-iso-propylsilyloxymethyl (TOM), and triisopropylsilyl (TIPS) ethers), methyl ethers, and ethoxyethyl ethers (EE) and the like. Suitable amine protecting groups include without limit carbobenzyloxy (Cbz); p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts), and other sulfonamides (e.g., Nosyl & Nps), and the like. A variety of protecting groups and the synthesis thereof may be found in "Protective Groups in Organic Synthesis" by T. W. Greene and P. G. M. Wuts, John Wiley & Sons, 2006.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the disclosure.

Example 1: Preparation of Hexyl 2-Hydroxy-4-(Methylthio)Butanoate

To a 4 neck 1 L round bottom flask fitted with a reflux condenser, dean stark trap, thermocouple, and mechanical overhead stirrer was added 2-hydroxy-4-(methylthio)butanoic acid (100 g, 666 mmol, obtained for example by stirring Alimet over activated charcoal, filtering and concentrating in a rotovap), 1-hexanol (125.4 mL, 999 mmol), sodium hydrogen sulfate (1.60 g, 13.32 mmol), and toluene (500 mL). The reaction was heated to reflux with removal of water (20 mL) during the course of about 5.5 hours and the reaction was monitored by GC analysis. The reaction was cooled to room temperature overnight and the organic layer was washed with saturated $NaHCO_3$ (1×250 mL), DI water (1×250 mL) and brine (2×250 mL), dried over sodium sulfate, filtered and evaporated to give a brown viscous liquid (253.3 g). The product was purified by kugelrohr distillation at 100° C. and 0.1 Torr vacuum to give a colorless viscous liquid (100.0 g, 64.1%). m/z 257 ($MNa^+$).

Example 2: Preparation of Hexyl 2-Hydroxy-4-(Methylsulfinyl)Butanoate

To a solution of hexyl 2-hydroxy-4-(methylthio)butanoate (5.03 g, 21.46 mmol) in dichloromethane at 0° C. was added m-chloroperoxybenzoic acid (mCPBA) portionwise over 20 min. The resulting mixture was allowed to warm to room temperature with stirring overnight. The reaction was washed with saturated sodium bicarbonate (3×100 mL), 1N HCl (1×80 mL), and brine (1×80 mL). The organic layer was dried over magnesium sulfate, filtered and evaporated to give ~6 g of a crude oil. The oil was purified by silica gel chromatography with 0-6% methanol/dichloromethane to give a viscous product (4.10 g, 76%). $^1$H NMR (500 MHz, chloroform-d) δ ppm 0.89 (t, J=6.68 Hz, 3H) 1.25-1.39 (m, 6H) 1.67 (quin, J=6.99 Hz, 2H) 2.05-2.17 (m, 1H) 2.32-2.42 (m, 1H) 2.56-2.63 (m, 3H) 2.72-2.97 (m, 2H) 3.34-3.44 (m, 1H) 4.15-4.24 (m, 2H) 4.26-4.36 (m, 1H). m/z 251 ($MH^+$).

Example 3: Preparation of Octyl 2-Hydroxy-4-(Methylthio)Butanoate

To a multi-neck 5 L round bottom flask fitted with a mechanical stirrer, reflux condenser, and dean stark trap was added 2-hydroxy-4-(methylthio)butanoic acid (650 g, 4.33 mol, obtained for example by stirring Alimet over activated charcoal, filtering and concentrating in a rotovap), 1-octanol (845.4 g, 6.49 mol), sodium hydrogen sulfate (10.4 g, 86 mmol), and toluene (2.7 L). The resulting solution was heated to reflux with removal of water (~146 mL) during the course of about 5.5 hours and the reaction was monitored by GC analysis. The reaction was cooled to room temperature overnight and then washed with saturated $NaHCO_3$ (1×1.5 L), DI water (1×1.5 L) and brine (1×1.5 L), dried over sodium sulfate, filtered and evaporated to give a dark viscous product (1,525 g). The product was purified by kugelrohr distillation at 130-150° C. and 0.1 mm Hg vacuum to give a pale yellow viscous liquid (507.6 g, 45%). m/z 285 ($MNa^+$).

Example 4: Preparation of Octyl 2-Hydroxy-4-(Methylsulfinyl)Butanoate

To a mixture of octyl 2-hydroxy-4-(methylthio)butanoate (50 g, 191 mmol) suspended in water (100 mL) was added 30% hydrogen peroxide (29 mL) and the mixture was stirred at 25° C. A mild exotherm was observed. The mixture became homogenous within an hour. Analysis indicated the reaction was completed within four hours. The mixture was extracted with EtOAc (200 mL). The organic phase was washed with a 10% sodium bisulfite solution (50 mL). The organic phase was dried with anhydrous magnesium sulfate and the solvent was removed by distillation with a rotary evaporator to give a colorless viscous liquid (51.4 g, 97%). $^1$H NMR (500 MHz, DMSO-$d_6$) δ ppm 0.87 (t, J=6.68 Hz, 3H) 1.14-1.38 (m, 10H) 1.49-1.69 (m, 2H) 1.77-1.96 (m, 1H) 1.96-2.17 (m, 1H) 2.43-2.61 (m, 4H) 2.63-2.76 (m, 1H) 2.77-2.90 (m, 1H) 3.96-4.13 (m, 2H) 4.13-4.29 (m, 1H) 5.64 (dd, J=5.72, 2.23 Hz, 1H). m/z 279 ($MH^+$).

Example 5: Preparation of Decyl 2-Hydroxy-4-(Methylthio)Butanoate

To a 4 neck 1 L round bottom flask fitted with a reflux condenser, dean stark trap, thermocouple, and mechanical overhead stirrer was added 2-hydroxy-4-(methylthio)butanoic acid (125 g, 832.2 mmol, obtained for example by stirring Alimet over activated charcoal, filtering and concentrating in a rotovap), 1-decanol (238 mL, 1248 mmol), sodium hydrogen sulfate (1.998 g, 16.64 mmol), and toluene (625 mL). The reaction was heated to reflux with removal of water (16 mL) during the course of about 6 hours and the reaction was monitored by GC analysis. The reaction was cooled to room temperature overnight and the organic layer was washed with saturated $NaHCO_3$ (1×300 mL), DI water (1×300 mL) and brine (2×300 mL), dried over sodium sulfate, filtered and evaporated to give an amber viscous liquid (395.5 g). The liquid product was purified by kugelrohr distillation at 110° C. and 0.1 Torr vacuum to give a viscous liquid (105.23 g, 43.5%). m/z 313 ($MNa^+$).

Example 6: Preparation of Decyl 2-Hydroxy-4-(Methylsulfinyl)Butanoate

To a solution of decyl 2-hydroxy-4-(methylthio)butanoate (20.05 g, 69.03 mmol) in dichloromethane (300 mL) at 0° C. was added mCPBA (77%, 14.7 g, 65.6 mmol) portionwise over 30 min. The resulting mixture was allowed to warm to room temperature with stirring overnight. Another portion of mCPBA (77%, 1.4 g, 6.25 mmol) was added to the solution at 0° C. and the resulting mixture was allowed to warm to room temperature with stirring over the weekend. The reaction was washed with 10% sodium bisulfite (2×100 mL), saturated sodium bicarbonate (3×150 mL), 1N HCl (1×150 mL), and brine (1×200 mL). The organic layer was dried over magnesium sulfate, filtered and evaporated to give a crude oil. The oil was purified by silica gel chromatography with 0-6% methanol/dichloromethane to give a light yellow viscous liquid (20.61 g, 97%). $^1$H NMR (500 MHz, DMSO-$d_6$) δ ppm 0.85 (t, J=6.83 Hz, 3H) 1.10-1.37 (m, 14H) 1.50-1.65 (m, 2H) 1.80-1.93 (m, 1H) 1.97-2.08 (m, 1H) 2.52

(d, J=3.81 Hz, 3H) 2.60-2.75 (m, 1H) 2.75-2.91 (m, 1H) 3.98-4.12 (m, 2H) 4.12-4.20 (m, 1H) 5.62 (dd, J=5.72, 2.54 Hz, 1H). m/z 307 (MH+).

Example 7: Preparation of
2-Hydroxy-4-(Methylthio)-N-Octylbutanamide

To a solution of 2-hydroxy-4-(methylthio)butanoic acid (50.74 g, 337.8 mmol, obtained by stirring Alimet over activated charcoal, filtering and concentrating in a rotovap) in dichloromethane (1 L) was added triethylamine (93 mL, 667.3 mmol) and the resulting mixture was cooled to 0° C. To the cooled mixture was added acetyl chloride (26 mL, 365.6 mmol) dropwise. The ice bath was removed and the reaction was allowed to warm to room temperature overnight. The reaction was washed with 1N HCl (2×300 mL), and brine (1×300 mL), dried over magnesium sulfate, filtered and evaporated to give an amber viscous liquid (59.82 g, 63.1%). m/z 193 (MH+).

To a solution of 2-acetoxy-4-(methylthio)butanoic acid (6.10 g, 31.7 mmol) in dichloromethane (100 mL) at 0° C. was added thionyl chloride (11.53 mL, 158.5 mmol) slowly over 30 min. The reaction was allowed to warm to room temperature with stirring overnight. The solvent was evaporated and the resulting oil was dried on the high vacuum for 3 hrs. To a solution of the resulting oil in dichloromethane (100 mL) at 0° C. was added triethylamine (8.84 mL, 63.4 mmol) and then octylamine (5.24 mL, 31.7 mmol) and the reaction was allowed to warm to room temperature with stirring overnight. The reaction was evaporated, redissolved in EtOAc (150 mL) and washed with 1N HCl (3×100 mL), saturated sodium bicarbonate (3×100 mL), and brine (1×100 mL). The organic layer was dried over magnesium sulfate, filtered and evaporated to give a viscous liquid. The liquid was purified by silica gel chromatography with 0-30% EtOAc/heptane to give a thick yellow liquid. (6.61 g, 69%). m/z 304 (MH+).

Example 8: Preparation of
2-Hydroxy-4-(Methylsulfinyl)-N-Octylbutanamide

To a solution of 4-(methylthio)-1-(octylamino)-1-oxobutan-2-yl acetate (6.33 g, 20.86 mmol) in dichloromethane (200 mL) at 0° C. was added mCPBA (77%, 4.67 g, 20.86 mmol). The resulting mixture was allowed to warm to room temperature with stirring overnight. The reaction was washed with saturated sodium bicarbonate (3×100 mL), 1N HCl (1×100 mL), and brine (1×100 mL). The organic layer was dried over magnesium sulfate, filtered and evaporated to give a thick yellow liquid (6.7 g, 100%). m/z 320 (MH+).

To a solution of 4-(methylsulfinyl)-1-(octylamino)-1-oxobutan-2-yl acetate (5.7 g, 17.87 mmol) in methanol (75 mL) was added 1M NaOH (26.8 mL, 26.8 mmol) and the resulting solution was stirred overnight. The reaction was evaporated to a small volume and treated with EtOAc (100 mL) and 1N HCl (100 mL). The layers were separated and the organic layer was dried over magnesium sulfate, filtered and evaporated. The crude material was purified by silica gel chromatography with 0-5% methanol/dichloromethane. The desired fractions were collected and evaporated to give a white solid (3.23 g, 65%). $^1$H NMR (500 MHz, DMSO-$d_6$) δ ppm 0.85 (t, J=6.83 Hz, 3H) 1.24 (br. s., 10H) 1.33-1.47 (m, 2H) 1.73-1.89 (m, 1H) 1.95-2.10 (m, 1H) 2.51 (d, J=0.64 Hz, 3H) 2.58-2.87 (m, 2H) 2.99-3.14 (m, 2H) 3.95 (dd, J=7.15, 4.29 Hz, 1H) 5.69 (d, J=5.09 Hz, 1H) 7.76 (t, J=5.40 Hz, 1H). m/z 278 (MH+).

Example 9: Preparation of
N-Decyl-2-Hydroxy-4-(Methylthio)Butanamide

To a solution of 2-acetoxy-4-(methylthio)butanoic acid (17.1 g, 89 mmol) in dichloromethane (350 mL) at 0° C. was added thionyl chloride (32.4 mL, 445 mmol) dropwise over 1 hr. The reaction was stirred at 0° C. for 1.5 hrs then the cooling bath was removed and the reaction was warmed to room temperature with stirring for 3 hrs. The solvent was evaporated and the resulting liquid was dried under high vacuum for 1 hr to give an orange viscous liquid. A solution of the resulting liquid in dichloromethane (~30 mL) was added to a solution of triethylamine (24.8 mL, 178 mmol) and decylamine (17.8 mL, 89 mmol) in dichloromethane (150 mL) at 0° C. and the reaction was allowed to warm to room temperature with stirring overnight. The reaction was evaporated, redissolved in EtOAc (300 mL) and washed with 1N HCl (3×150 mL), saturated sodium bicarbonate (3×150 mL), and brine (1×150 mL). The organic layer was dried over magnesium sulfate, filtered and evaporated to give a viscous liquid. The liquid product was purified by silica gel chromatography with 0-40% EtOAc/heptane to give a yellow viscous liquid. (21.1 g, 71%). m/z 332 (MH+).

Example 10: Preparation of
N-Decyl-2-Hydroxy-4-(Methylsulfinyl)Butanamide

To a solution of 1-(decylamino)-4-(methylthio)-1-oxobutan-2-yl acetate (21.1 g, 63.4 mmol) in methanol (110 mL) at 0° C. was added hydrogen peroxide (30%, 19.43 mL, 190 mmol) and the ice bath was removed. The reaction was allowed to stir for 5.5 hr. The reaction was diluted with water (400 mL) and then extracted with EtOAc (200 mL) to give an emulsion which did not separate after 18 hrs. The emulsion was treated with brine (250 mL) and the layers separated. The aqueous layer was extracted with EtOAc (200 mL) and the combined organic layers were washed with 10% sodium bisulfite. The organic layer was dried over magnesium sulfate, filtered and evaporated to give an orange viscous liquid (22.4 g, 100%). m/z 348 (MH+).

To a solution of 1-(decylamino)-4-(methylsulfinyl)-1-oxobutan-2-yl acetate (22.4 g, 63.4 mmol) in methanol (300 mL) was added 2.5 N NaOH (39 mL, 97.5 mmol) and the resulting solution was stirred at room temperature for 5 hrs. The reaction was quenched with concentrated HCl (12.5 mL) and then evaporated to a small volume. The resulting mixture was treated with EtOAc (200 mL) and then washed with 1N HCl (150 mL), saturated sodium bicarbonate (50 mL), dried over magnesium sulfate, filtered and evaporated to give a solid. The solid was dissolved in dichloromethane and purified by silica gel chromatography with 0-10% methanol/dichloromethane. The desired fractions were collected and evaporated to give a white solid (13.6 g, 70%). $^1$H NMR (500 MHz, DMSO-$d_6$) δ ppm 0.85 (t, J=6.83 Hz, 3H) 1.15-1.32 (m, 14H) 1.32-1.46 (m, 2H) 1.75-1.87 (m, 1H) 1.94-2.06 (m, 1H) 2.51 (d, J=1.27 Hz, 3H) 2.58-2.88 (m, 2H) 3.00-3.12 (m, 2H) 3.89-4.02 (m, 1H) 5.69 (d, J=5.40 Hz, 1H) 7.76 (t, J=5.56 Hz, 1H). m/z 306 (MH+).

Example 11: Preparation of Methyl
2-Hydroxy-4-(Methylsulfinyl)Butanoate

To a solution of methyl 2-hydroxy-4-(methylthio)butanoate (130.2 g, 92.7 mmol) in DCM (460 mL) was added 30% hydrogen peroxide (101.2 mL, 990.9 mmol) applying cooling as needed with an ice bath while keeping the reaction temperature between 20-28° C. The reaction was allowed to stir at room temperature overnight. To the reaction was added solid sodium sulfite (~60 g) portion wise keeping the temperature less than 25° C. by cooling with an ice bath as needed. When the quench was complete as judged by peroxide test strip, the layers were separated (multiple layers observed) and the top two phases were dried over magnesium sulfate, filtered and evaporated to give a yellow viscous liquid (111.5 g, 78% yield). M/z=181 (M$^+$H$^+$).

Example 12: Preparation of Isopropyl 2-Hydroxy-4-(Methylsulfinyl)Butanoate

To a solution of isopropyl 2-hydroxy-4-(methylthio)butanoate (136.8 g, 711.5 mmol) in DCM (500 mL) was added 30% hydrogen peroxide (90.8 mL, 889.4 mmol) applying cooling as needed with an ice bath while keeping the reaction temperature between 20-28° C. The reaction was allowed to stir at room temperature over 2 nights. To the reaction was added solid sodium sulfite (36.6 g) portion wise keeping the temperature less than 25° C. by cooling with an ice bath as needed. When the quench was complete as judged by peroxide test strip, the layers were separated and the organic phase was dried over magnesium sulfate, filtered and evaporated to give a light yellow viscous liquid (147.4 g, 99% yield). M/z=209 (M$^+$H$^+$).

Example 13: Preparation of Butyl 2-Hydroxy-4-(Methylthio)Butanoate

To a 4 neck round bottom flask fitted with a reflux condenser, dean stark trap, and mechanical overhead stirrer was added 2-hydroxy-4-(methylthio)butanoic acid (100 g, 666 mmol), 1-butanol (91.38 mL, 999 mmol), sodium hydrogen sulfate (1.60 g, 13.32 mmol), and toluene (500 mL). The reaction was heated to reflux with removal of water (19 ml) during the course of ~5 hours and the reaction was monitored by GC analysis. The reaction mixture was cooled to room temperature overnight and then the organic layer was washed with sat. NaHCO$_3$ (1×250 ml), DI water (1×250 ml), and brine (2×250 ml), dried over sodium sulfate, filtered and evaporated to give a brown viscous liquid (178.7 g). The liquid product was purified by kugelrohr distillation increasing temperature to 75° C. and 0.1 Torr vacuum to give a yellow viscous liquid (85.69 g, 62.3%). m/z 229 (MNa$^+$).

Example 14: Preparation of Butyl 2-Hydroxy-4-(Methylsulfinyl)Butanoate

To a solution of butyl 2-hydroxy-4-(methylthio)butanoate (5.0 g, 24.2 mmol) in dichloromethane (150 mL) at 0° C. was added mCPBA (77%, 5.43 g, 24.2 mmol) portion-wise over 1 hour. The resulting mixture was allowed to warm to room temperature with stirring overnight. The reaction was washed with sat. sodium bicarbonate (3×100 mL), 1N HCl (1×100 mL), and brine (1×100 mL). The organic layer was dried over magnesium sulfate, filtered and evaporated to give ~3 g of a thick liquid. The liquid product was purified by silica gel chromatography on a 90 g column with 0-5% methanol/dichloromethane over 10 CV. The desired fractions were collected and evaporated to give a thick liquid (2.22 g, 41%).

Example 15: Preparation of Decyl 2-Hydroxy-4-(Methylsulfonyl)Butanoate

To a solution of decyl 2-hydroxy-4-(methylthio)butanoate (1.01 g, 3.47 mmol) in dichloromethane (25 mL) at 0° C. was added mCPBA (77%, 1.17 g, 5.22 mmol). The resulting mixture was allowed to warm to room temperature with stirring over the weekend. Another portion of mCPBA (77%, 0.4 g, 1.78 mmol) was added to the solution at 0° C. and the resulting mixture was allowed to warm to room temperature with stirring overnight. The reaction was washed with 10% sodium bisulfite (1×50 mL), sat. sodium bicarbonate (3×50 mL), and brine (1×50 mL). The organic layer was dried over magnesium sulfate, filtered and evaporated to give a solid. The solid was dissolved in a small amount of DCM and purified by silica gel chromatography on a 40 g column with 0% methanol/dichloromethane over 1 column volume (CV), then 0-5% methanol/dichloromethane over 8 CV. The desired fractions were collected and evaporated to give a white solid (1.03 g, 92%).

Example 16: Preparation of Octyl 2-Hydroxy-4-(Methylsulfonyl)Butanoate

A solution of octyl 2-hydroxy-4-(methylsulfinyl)butanoate (505 mg, 1.81 mmol) in ethyl acetate (10 mL) was cooled on an ice bath and treated with peracetic acid (32%, 0.57 mL, 2.71 mmol). The ice bath was removed and the solution was stirred at room temperature overnight. The solution was then cooled on an ice bath and quenched with 3 mL of 10% sodium sulfite solution. The layers were separated and the organic layer was washed with saturated sodium carbonate (2×10 mL), brine (1×10 mL). The organic layer was evaporated to give a white solid. M/z=295 (M$^+$H$^+$).

Example 17: Preparation of Dodecyl 2-Hydroxy-4-(Methylsulfonyl)Butanoate

A solution of dodecyl 2-hydroxy-4-(methylsulfinyl)butanoate (545 mg, 1.63 mmol) in ethyl acetate (10 mL) was cooled on an ice bath and treated with peracetic acid (32%, 0.51 mL, 2.42 mmol). The ice bath was removed and the solution was stirred at room temperature overnight. The solution was then cooled on an ice bath and quenched with 3 mL of 10% sodium sulfite solution. The layers were separated and the organic layer was washed with saturated sodium carbonate (2×10 mL), and brine (1×10 mL). The organic layer was evaporated to give a white solid (420 mg, 70%). M/z=351 (M$^+$H$^+$).

Example 18: Properties of Isopropyl 2-Hydroxy-4-(Methylsulfinyl)Butanoate

Isopropyl 2-hydroxy-4-(methylsulfinyl)butanoate (also called iC3SO) has the following properties.

TABLE 1

| Solvent properties of iC3SO | |
|---|---|
| Molecular Weight | 208 g/mol |
| Density | 1.17 g/mL |
| Boiling Point | 248° C. |
| Flash Point | 194° C. |
| Freezing Point | <−90° C. |
| Viscosity | 519 cps |

Example 19: Use of Octyl 2-Hydroxy-4-(Methylsulfinyl)Butanoate in Hard Surface Cleaners or Degreasers Green or regular hard surface cleaner or degreaser formulations containing commercial surfactants or a mixture (i.e., monomers, dimers, and short oligomers) of octyl 2-hydroxy-4-(methylsulfinyl)butanoate (also called "C8SO") were formulated, as shown in Table 2 below. The density of C8SO is 1.08 g/mL.

TABLE 2

Compositions of Hard Surface All Purpose Cleaners and Hard Surface Degreasers

| Type | Reference | Test |
| --- | --- | --- |
| Green All Purpose | 1% Soda ash, 1% C8-14 alkyl polyglucoside | 1% Soda ash, 1% C8SO |
| Regular All Purpose | 0.5% Soda ash, 1% Na alkylbenzene sulfonate (LAS), 1% C9-11 alcohol 6 mole ethoxylate | 0.5% Soda ash, 1% Na linear alkylbenzene sulfonate (LAS), 1% C8SO |
| Green Degreaser | 1% Soda ash, 1% C9-11 alcohol 6 mole ethoxylate | 1% Soda ash, 1% C8SO |
| Regular Degreaser | 2% Dipropylene glycol methyl ether, 1% C9-11 alcohol 6 mole ethoxylate | 2% Dipropylene glycol methyl ether, 1% C8SO |

The formulations were tested using ASTM Methods D-4488, Standard Guide for Testing Cleaning Performance of Products Intended for Use on Resilient Flooring and Washable Walls. For the D-4488 A-2 greasy soil/painted Masonite wallboard test method, the substrate was ⅛" wallboard cut into 4" by 4" tiles. The tiles were painted by roller with latex paint (i.e., BEHR Premium Plus, Ultra-Pure Flat White). Two coats were applied and the tiles were aged overnight at 50° C. The soil was a blend of 33 g vegetable oil, 33 g vegetable shortening, 33 g lard, and 0.2 g carbon black. The tiles were weighed before and after applying the soil for uniformity (approximately 0.4 g soil/tile). Soil was held at 60° C. and applied with a cheesecloth. The soiled panels were aged overnight at ambient conditions. For testing, 15 g of each formulation as-is (i.e., no dilution) was applied to a prewet sponge. The apparatus used was Gardner Straight-Line Washability Apparatus. The tests were run for 10 cycles. Reflectance on the "Y" scale was determined for each tile before applying the soil and after cleaning. Because of the nature of the soil, an average was determined from tiles not used in the testing.

For the D-4488 A-5 particulate and oily soil/vinyl tiles test method, the substrate was ⅛" white vinyl floor tiles was cut into 8" by 4" tiles. The soil was 50 mg of particulate soil and 5 drops of oily blend per formula in the method. Soil was applied with a paper towel and aged overnight at ambient conditions. For testing, 70 mL of formulation as-is (i.e., no dilution) was applied to a prewet sponge. The apparatus used was Gardner Straight-Line Washability Apparatus. The tests were run for 10 cycles. Reflectance on the "L" scale was determined for each tile before applying the soil, after applying the soil, and after cleaning.

Tests were run in quadruplicate for both methods and results averaged. Outliers were discarded using Dixon's Q test at 90% confidence. The Students T Test was used to estimate the p value and the numbers reported are the probabilities that the differences are random. The values for the test formulation were considered different from the values for the reference formulation if the probability was less than 5%. The results are presented in Tables 3 and 4.

TABLE 3

Performance of Hard Surface All Purpose Cleaners (ASTM 4488 A-5)

| Formulation | Soil Removal | Significantly different from reference | P value |
| --- | --- | --- | --- |
| Green Reference | 95.1% | | |
| Green Test | 94.0% | Yes | 4.78% |
| Regular Reference | 87.3% | | |
| Regular Test | 87.2% | No | 94.66% |

TABLE 4

Performance of Hard Surface Degreasers (ASTM 4488 A-2)

| Formulation | Soil Removal | Significantly different from reference | P value |
| --- | --- | --- | --- |
| Green Reference | 65.3% | | |
| Green Test | 69.6% | No | 38.46% |
| Regular Reference | 74.5% | | |
| Regular Test | 82.0% | Yes | 2.15% |

The performance of each test formulation was similar to that of the reference formulation. Thus, the C8SO compounds have solvent properties similar to standard surfactants used in hard surface cleaners or degreasers.

Example 20: Aqueous Solubility

The aqueous solubility of various compounds was determined in water at 25° C. and atmospheric pressure. Table 5 presents the results.

TABLE 5

Solubility in Water

| Compound | Solubility (wt/wt total) |
| --- | --- |
| Hexyl 2-hydroxy-4-(methylsulfinyl)butanoate- | >50.0 wt % |
| Octyl 2-hydroxy-4-(methylsulfinyl)butanoate | >50.0 wt % |
| N-Octyl-2-hydroxy-4-(methylsulfinyl)butanamide | >50.0 wt % |
| Isopropyl 2-hydroxy-4-(methylthio)butanoate | 2.5 wt % |
| Butyl 2-hydroxy-4-(methylthio)butanoate | 0.9 wt % |
| Decyl 2-hydroxy-4-(Methylsulfonyl)butanoate | <0.1 wt % |
| Methyl 2-hydroxy-4-(methylsulfinyl)butanoate | >50% wt %* |
| Isopropyl 2-hydroxy-4-(methylsulfinyl)butanoate | >50% wt %* |
| Butyl 2-hydroxy-4-(methylsulfinyl)butanoate | >50% wt %* |

*Theoretical

What is claimed is:

1. A method for using a compound of Formula (I) as a solvent, the method comprising contacting at least one compound of Formula (I) with at least one solute to form a solution, the compound of Formula (I):

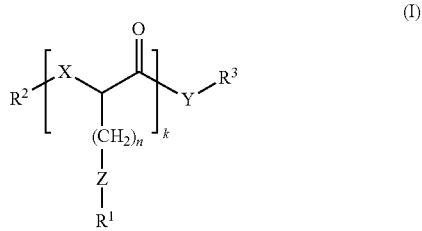

wherein:

$R^1$ is hydrocarbyl or substituted hydrocarbyl;

R² is hydrogen, hydrocarbyl, or substituted hydrocarbyl;

R³ is an aliphatic moiety having from one to twelve carbons in the principal chain when Z is S or SO₂, or an aliphatic moiety having from one to five carbons in the principal chain when Z is SO;

X and Y independently are O or NH;

Z is S, SO, or SO₂;

k is an integer of 1 or greater; and n is an integer of 1 or greater;

wherein the at least one solute is a herbicide, a fungicide, an insecticide, a pigment, an enzyme, a surfactant, a fragrance, or a combination thereof.

2. The method of claim 1, wherein R¹ is alkyl, substituted alkyl, aryl, or substituted aryl; R² is hydrogen, alkyl, substituted alkyl, aryl, substituted aryl, acyl, $(CH_2CH_2O)_pH$, $(CH_2CH(CH_3)O)_pH$, or a combination of $(CH_2CH_2O)_pH$ and $(CH_2CH(CH_3)O)_pH$, p is an integer of 1 or greater; and k is 1, 2, 3, 4, 5, 6, or a combination thereof.

3. The method of claim 2, wherein R³ is $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, or $C_1$-$C_{12}$ substituted alkynyl and Z is S or SO₂, or R³ is $C_1$-$C_5$ alkyl, $C_1$-$C_5$ substituted alkyl, $C_1$-$C_5$ alkenyl, $C_1$-$C_5$ substituted alkenyl, $C_1$-$C_5$ alkynyl, or $C_1$-$C_5$ substituted alkynyl and Z is SO.

4. The method of claim 1, wherein R¹ is methyl; R² is hydrogen; R³ is $C_1$ to $C_8$ alkyl or $C_1$ to $C_8$ substituted alkyl; X is oxygen; Y is oxygen or nitrogen; Z is sulfur; and n is 2.

5. The method of claim 1, wherein R¹ is methyl; R² is hydrogen; R³ is $C_1$ to $C_5$ alkyl or $C_1$ to $C_5$ substituted alkyl; X is oxygen; Y is oxygen or nitrogen; Z is sulfoxide; and n is 2.

6. The method of claim 1, wherein the solution further comprises a binder, another solvent, a wetting agent, a thickening agent, a foam control agent, a dispersant, a filler, a disintegrant, a color agent, a hydrotrope, a linker, a pH regulating agent, a chelating agent, a preservative, an optical brightening agent, a bleaching, a scale inhibitor, a water softening agent, or combination thereof.

7. The method of claim 1, wherein the at least one compound of Formula (I) and the at least one solute are present at a volume to mass ratio from about 1:1 to about 100:1.

8. The method of claim 1, wherein the solution is a home care product, a fabric care product, a personal care product, an industrial cleaner, an institutional cleaner, an agricultural product, a landscaping product, a paint formulation, or a coating formulation.

9. A composition comprising at least one compound of Formula (I) and at least one agent, the compound of Formula (I):

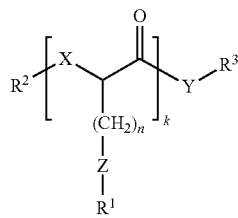

wherein:

R¹ is hydrocarbyl or substituted hydrocarbyl;

R² is hydrogen, hydrocarbyl, or substituted hydrocarbyl;

R³ is an aliphatic moiety having from one to twelve carbons in the principal chain when Z is S or SO₂, or an aliphatic moiety having from one to five carbons in the principal chain when Z is SO;

X and Y independently are O or NH;

Z is S, SO, or SO₂;

k is an integer of 1 or greater; and n is an integer of 1 or greater;

wherein the at least one agent is a herbicide, a fungicide, an insecticide, a pigment, an enzyme, a surfactant, a fragrance, or a combination thereof.

10. The composition of claim 9, wherein R¹ is alkyl, substituted alkyl, aryl, or substituted aryl; R² is hydrogen, alkyl, substituted alkyl, aryl, substituted aryl, acyl, $(CH_2CH_2O)_pH$, $(CH_2CH(CH_3)O)_pH$, or a combination of $(CH_2CH_2O)_pH$ and $(CH_2CH(CH_3)O)_pH$, p is an integer of 1 or greater; and k is 1, 2, 3, 4, 5, 6, or a combination thereof.

11. The composition of claim 10, wherein R³ is $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, or $C_1$-$C_{12}$ substituted alkynyl and Z is S or SO₂, or R³ is $C_1$-$C_5$ alkyl, $C_1$-$C_5$ substituted alkyl, $C_1$-$C_5$ alkenyl, $C_1$-$C_5$ substituted alkenyl, $C_1$-$C_5$ alkynyl, or $C_1$-$C_5$ substituted alkynyl and Z is SO.

12. The composition of claim 9, wherein R¹ is methyl; R² is hydrogen; R³ is $C_1$ to $C_8$ alkyl or $C_1$ to $C_8$ substituted alkyl; X is oxygen; Y is oxygen or nitrogen; Z is sulfur; and n is 2.

13. The composition of claim 9, wherein R¹ is methyl; R² is hydrogen; R³ is $C_1$ to $C_5$ alkyl or $C_1$ to $C_5$ substituted alkyl; X is oxygen; Y is oxygen or nitrogen; Z is sulfoxide; and n is 2.

14. The composition of claim 9, wherein the composition further comprises a binder, another solvent, a wetting agent, a thickening agent, a foam control agent, a dispersant, a filler, a disintegrant, a color agent, a hydrotrope, a linker, a pH regulating agent, a chelating agent, a preservative, an optical brightening agent, a bleaching agent, a scale inhibitor, a water softening agent, or a combination thereof.

15. The composition of claim 9, wherein the composition is a home care product, a fabric care product, a personal care product, an industrial cleaner, an institutional cleaner, an agricultural product, a landscaping product, a paint formulation, or coating formulation.

16. A method for preparing a composition, the method comprising contacting at least one agent with at least one compound of Formula (I) to form the composition, the compound of Formula (I):

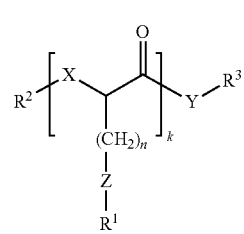

wherein:

R¹ is hydrocarbyl or substituted hydrocarbyl;

R² is hydrogen, hydrocarbyl, or substituted hydrocarbyl;

R³ is an aliphatic moiety having from one to twelve carbons in the principal chain when Z is S or $SO_2$, or an aliphatic moiety having from one to five carbons in the principal chain when Z is SO;

X and Y independently are O or NH;

Z is S, SO, or $SO_2$;

k is an integer of 1 or greater; and n is an integer of 1 or greater;

wherein the at least one agent is a herbicide, a fungicide, an insecticide, a pigment, an enzyme, a surfactant, a fragrance, or a combination thereof.

17. The method of claim 16, wherein $R^1$ is alkyl, substituted alkyl, aryl, or substituted aryl; $R^2$ is hydrogen, alkyl, substituted alkyl, aryl, substituted aryl, acyl, $(CH_2CH_2O)_pH$, $(CH_2CH(CH_3)O)_pH$, or a combination of $(CH_2CH_2O)_pH$ and $(CH_2CH(CH_3)O)_pH$, p is an integer of 1 or greater; and k is 1, 2, 3, 4, 5, 6, or a combination thereof.

18. The method of claim 17, wherein $R^3$ is $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, or $C_1$-$C_{12}$ substituted alkynyl and Z is S or $SO_2$, or $R^3$ is $C_1$-$C_5$ alkyl, $C_1$-$C_5$ substituted alkyl, $C_1$-$C_5$ alkenyl, $C_1$-$C_5$ substituted alkenyl, $C_1$-$C_5$ alkynyl, or $C_1$-$C_5$ substituted alkynyl and Z is SO.

19. The method of claim 16, wherein $R^1$ is methyl; $R^2$ is hydrogen; $R^3$ is $C_1$ to $C_8$ alkyl or $C_1$ to $C_8$ substituted alkyl; X is oxygen; Y is oxygen or nitrogen; Z is sulfur; and n is 2.

20. The method of claim 16, wherein $R^1$ is methyl; $R^2$ is hydrogen; $R^3$ is $C_1$ to $C_5$ alkyl or $C_1$ to $C_5$ substituted alkyl; X is oxygen; Y is oxygen or nitrogen; Z is sulfoxide; and n is 2.

21. The method of claim 16, wherein the composition further comprises a binder, another solvent, a wetting agent, a thickening agent, a foam control agent, a dispersant, a filler, a disintegrant, a color agent, a hydrotrope, a linker, a pH regulating agent, a chelating agent, a preservative, an optical brightening agent, a bleaching agent, a scale inhibitor, a water softening agent, or a combination thereof.

22. The method of claim 16, wherein the composition is a home care product, a fabric care product, a personal care product, an industrial cleaner, an institutional cleaner, an agricultural product, a landscaping product, a paint formulation, or a coating formulation.

* * * * *